United States Patent [19]

Pech

[11] Patent Number: 4,668,916

[45] Date of Patent: May 26, 1987

[54] LIQUID CRYSTAL NON-DESTRUCTIVE INSPECTION OF NON-FERROUS METALS

[75] Inventor: Gregory J. Pech, Littleton, Colo.

[73] Assignee: The United States of America as represented by the Secretary of the Air Force, Washington, D.C.

[21] Appl. No.: 744,593

[22] Filed: Jun. 14, 1985

[51] Int. Cl.⁴ .................. G01N 27/61; G02F 1/13
[52] U.S. Cl. .................. 324/456; 324/216; 350/331 R
[58] Field of Search .......... 324/456, 214–216, 324/96, 158 R; 350/331 R, 351, 374, 391; 356/237

[56] References Cited

U.S. PATENT DOCUMENTS

| | | | |
|---|---|---|---|
| 2,499,467 | 3/1950 | DeForest et al. | 175/183 |
| 2,669,692 | 2/1954 | Pearson | 324/456 X |
| 2,678,420 | 5/1954 | DeForest et al. | 324/32 |
| 3,097,337 | 7/1963 | Polin | 324/32 |
| 3,693,084 | 9/1972 | Augustine | 350/351 X |
| 3,803,485 | 4/1974 | Crites et al. | 324/65 R |
| 3,826,917 | 7/1974 | Molina | 250/302 |
| 3,889,053 | 6/1975 | Lloyd et al. | 350/351 X |
| 3,934,199 | 1/1976 | Channin | 324/158 R |
| 4,006,414 | 2/1977 | Parker | 350/351 X |
| 4,321,534 | 3/1982 | Mlot-Fijalkowski | 324/216 |
| 4,341,997 | 7/1982 | Borrows | 324/215 |
| 4,355,278 | 10/1982 | Burns et al. | 350/331 R X |

Primary Examiner—Gerard R. Strecker
Attorney, Agent, or Firm—Gerald B. Hollins; Donald J. Singer

[57] ABSTRACT

A non-destructive inspection arrangement for ferrous and non-ferrous metallic workpieces. The inspection arrangement employs a liquid crystal indicator medium and electrical current flow through the workpiece to develop potential differences across work surface flaws that are to be detected. The concepts of direct application of the liquid crystal medium to the work area surface and containment of the liquid cyrstal medium within a viewing device are also included.

13 Claims, 3 Drawing Figures

LIQUID CRYSTAL NON-DESTRUCTIVE INSPECTION OF NON-FERROUS METALS

RIGHTS OF THE GOVERNMENT

The invention described herein may be manufactured and used by or for the Government of the United States for all governmental purposes without the payment of any royalty.

BACKGROUND OF THE INVENTION

This invention relates to the field of visually inspecting ferrous and non-ferrous workpiece surfaces.

The use of visual inspection techniques for determining the condition of a smooth work surface is a common practice in the metal art. Such visual inspection can be used to ascertain the condition and quality of the surface being inspected and can also be used to detect the presence of deep-seated flaws as might result from fatigue cracking, manufacturing defects or other potential failure mechanisms in a workpiece. The detection of failure initiation sites is, of course, of vital importance in the maintenance of aircraft and in the vertification of aircraft components such as wing spar members, engine mounts, airframe surface components, and other highly stressed load carrying members. In industrial and aerospace applications, the use of visual inspection aided by a magnetic field and a suspension of magnetic particles has been routinely employed with ferrous members such as engine components and machine elements; such magnetic techniques are, however, ineffective for the non-ferrous metals commonly used in many structural elements.

The patent art includes several examples of visual inspection techniques wherein media of diverse types are employed as an inspection aid; this art includes the patent of Orlando G. Molina, U.S. Pat. No. 3,826,917, which concerns a magnetic inspection arrangement, the use of non-fluorescent magnetic particles suspended in a liquid medium, and visual inspection under fluorescent or ultraviolet light to provide an image contrasted against a fluorescent background. The use of magnetic particles contrasted against a fluorescent background achieves a high sensitivity inspection arrangement at lower cost than does the background absent fluorescent magnetic particle method that preceded the Molina patent. The Molina apparatus also includes a disclosure of suitable materials for use as a paint or colored coating covering for a material to be inspected. Since a modified version of the Molina color coating can also be employed with the present invention, the disclosure of the Molina patent is hereby incorporated by reference into the present specification.

The patent art also includes the method of detecting surface discontinuities described in the patent of Taber de Forest et al, U.S. Pat. No. 2,499,467, which is concerned with the detection of surface discontinuities in workpieces having relatively low electrical conductivity. The de Forest invention contemplates the use of electrostatic forces and the action of such forces on charged particles of small dimension located in an oil, alcohol or other liquid suspension. The de Forest invention also contemplates use of air suspended particles and the application of suspended particles by means of a brush. In the de Forest invention, a conductive backing member located on the back side of the object being tested is imparted with an electrostatic charge. This charge provides an attraction for charged, liquid suspended particles and the magnitude of this attraction varies at the locus of surface discontinuities in the workpiece.

Another patent, issued to Taber de Forest, U.S. Pat. No. 2,678,420, discloses the use of finely-divided particles and background enhancement for detecting flaws in a workpiece. This patent uses electrostatic attraction of the particles and physical disturbance of the workpiece, as by striking with a hammer for example, in order that mechanical movement of flaw edges can displace an otherwise uniform layer of particles and identify the flaw location.

The inspection patent art also includes the patent of Adolf Mlot-Fijalkowski et al, U.S. Pat. No. 4,321,534, which concerns a magnetizable workpiece, fluorescent magnetic particles, contrasting colors, a liquid suspension and a hydrophobic coating having no affinity for water, used in the detection of tears and faults in a workpiece. Both the workpiece and the applied particles are magnetic in nature in the Fijalkowski invention.

The patent art also includes the invention of Kenneth P. Borrows, in U.S. Pat. No. 4,341,997, which describes a particle inspection arrangement using a coated ferromagnetic particle suspension illuminated by simultaneously applied ultraviolet and white light. A notable feature of the Borrows invention is an ability to provide relatively bright indications of flaw presence and thereby enable inspection without the greatly diminished ambient lighting commonly required in fluorescent inspections.

The use of an electrical current flow in a fatigue crack detecting arrangement is shown in the patent of Nelson A. Crites et al, U.S. Pat. No. 3,803,485, wherein fatigue cracks are automatically located by crack propagation through a detector coating material. Crites also uses a conductive solution that propagates between a fatigue cracked metal member and a conductive layer comprising part of a detection coating. According to the Crites et al invention a reservoir of conductive liquid is fabricated into the detection coating and the rupture of this reservoir by a propagating fatigue crack provides a conductive path across an insulating barrier in the detecting coating.

The inspection art also includes U.S. Pat. No. 3,097,337, issued to H.S. Polin, concerning electroluminescent non-destructive flaw detection. The Polin invention contemplates use of a particulate material such as a metallic sulfide applied to a workpiece either by dusting or in a volatile hydrocarbon vehicle such as alcohol and energized into the light emitting state by a changing electrical field. The Polin invention also contemplates collection of electroluminescent particles within a surface flaw and their production of light energy in response to changes in the applied electrical field. The Polin electrical field changes may result from pulsating DC energy or alternating current energy; the location of these electric fields is controlled by movement of portable current applying probes around the surface of the workpiece being inspected.

The use of a liquid crystal device in combination with the electric field perturbations resulting from surface flaw conductivity variations in a workpiece is not disclosed in these examples of prior inspection techniques.

SUMMARY OF THE INVENTION

An object of the present invention is to provide a nondestructive inspection (NDI) arrangement which is applicable to all metals, magnetic and non-magnetic.

Another object of the invention is to provide an NDI inspection arrangement which is responsive to small workpiece flaws.

Another object of the invention is to provide an NDI inspection arrangement which utilizes the advantages of liquid crystal detection particles.

Another object of the invention is to provide an NDI inspection method which can be used with relatively low cost and simple apparatus.

Another object of the invention is to provide an NDI inspection arrangement which can be embodied as a self-contained combination of sensing elements or as a locally assembled collection of elements capable of improved detection characteristics.

Additional objects and features of the invention will be understood from the following description and the accompanying drawings.

These and other objects of the invention are achieved by disposing a suspension of liquid crystal particles over an optical contrast background located in contiguum with a work area surface of a workpiece, establishing an electrical potential difference across the workpiece work area surface, illuminating the work area liquid crystal suspension with visible spectrum optical energy, and visually inspecting the optical image reflected by the liquid crystal suspension and the optical contrast background for electric potential induced liquid crystal pattern perturbations, such perturbations identifying work area surface defects.

DETAILED DESCRIPTION

Figure 1:
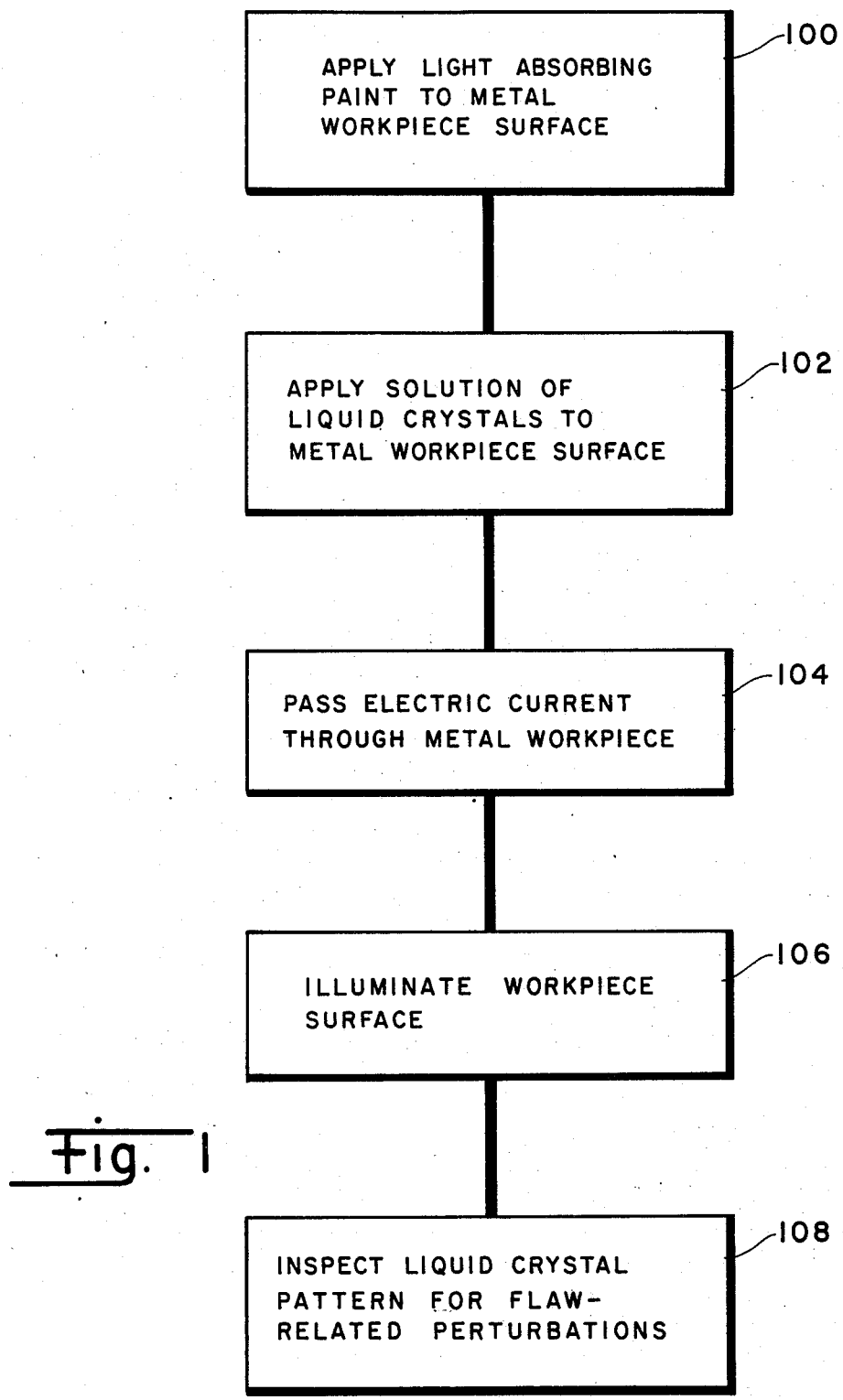
FIG. 1 is a block diagram of an NDI inspection sequence in accordance with the present invention.

Non-destructive inspection (NDI) techniques are desirable for achieving quality assurance and remaining life assurance without resort to the sample destruction or sample degradation techniques requiring replacement of the tested item. In the periodic inspection of aircraft components such as landing gear elements, wing attachment elements, and engine mounts, the use of NDI techniques for assisting the detection of fatigue cracks or other evidence of impending failure is especially desirable—replacement of such elements is often unnecessary in the absence of these detectable manifestations of impending failure. In a similar manner, the inspection of welds, forgings, castings, and rolled structural shapes is also enhanced by the use of non-destructive inspection techniques which allow use or re-use of the inspected member following the NDI operation. Existing NDI techniques, although economical and desirable for such inspections, are found to have limitations which often necessitate supplemental destructive testing for obtaining quantitative quality assurance information. The proof test requirement in pressure vessels is one example of such supplemental destructive testing that is frequently required. The application of liquid crystal display technology to NDI inspections can provide a higher resolution improvement in existing NDI procedures.

A solution or suspension of liquid crystals such as is commonly used in numerical displays for watches and hand calculators performs in the nature of a common venetian blind. In the presence of an electric field, the crystals in such a solution or suspension align in an ordered arrangement allowing light to pass through the crystals to then be either absorbed or reflected by a backing material that is located behind the crystal liquid and is contrasting in color with respect to the color of the liquid crystal solution itself. In this arrangement of a liquid crystal cell, the crystals not exposed to the electric field assume a random orientation and are thereby opaque or reflective to the incident light; such crystals assume a color which can be made contrasting with the background material color. In the usual arrangement of a liquid crystal cell, the background material is made to be black or light absorbing, while the randomly oriented crystal solution or suspension appears gray or metallic in color so the displayed information appears in the form of black characters on a gray field.

The present invention contemplates the application of liquid crystal techniques to the non-destructive inspection of metals. In accordance with this concept, the metallic workpiece is made to conduct an electrical current of preferably DC or direct current nature, and flaws in the work area surface are detected by perturbations or disturbances of an adjacent liquid crystal cell pattern caused by perturbations or disturbances of the electric field attending the current flow. The electric field perturbations are provided by interruption of uniform current flow in the work area surface where the current flow encounters a physical interruption of the flow path such as may be caused by a detectable flaw, inclusion, or crack; in short, electric field pattern perturbations result in corresponding perturbations of the liquid crystal pattern.

FIG. 1 of the drawings describes a sequence for applying the present invention to a workpiece such as a horizontally disposed flat plate. The FIG. 1 described sequence can, of course, be varied to suit other workpiece forms, as will be apparent from the following description.

The FIG. 1 sequence includes five steps which are identified by the blocks 100, 102, 104, 106, and 108. In the block 100, a light absorbing or black colored material such as paint or dye is applied to a work area surface region of a metal workpiece in order to provide the light absorbing background which will become visible through the aligned liquid crystal "venetian blind". In lieu of the indicated black paint, a dark colored anodizing or a dark coloration made in accordance with the procedures outlined in the above incorporated-by-reference Molina U.S. Pat. No. 3,826,917 may be employed.

In block 102 of FIG. 1, a solution or suspension of liquid crystal material is applied to the darkened workpiece surface. This application can be achieved by simple mechanical dispersion techniques such as spraying, painting, or by other dispersion arrangements which are known in the liquid coating art.

Block 104 in the FIG. 1 sequence calls for the establishment of an electric current through the metallic workpiece. This current should preferably flow in the body of the workpiece in a direction parallel to the work area surface, and in most arrangements would be oriented in the direction of right to left or forward and backward or some combination thereof with respect to the operator or inspector. Electrodes capable of establishing the desired current can be applied to the workpiece at opposite boundaries of the work area surface or at other peripheral workpiece locations—as an implied part of the block 104 step or in a preliminary step preceding the FIG. 1 sequence. Electrodes for achieving the desired current flow may be attached to the workpiece by clamps or spring loaded devices, or by welding, brazing, soldering, drilling and tapping, or other attachment means which are known in the art. For use with aircraft members and others carefully dimensioned parts, the use of spring loaded attachments or the use of existing perforations or other non-destructive electrode attachments is preferred.

The current flow desired in the workpiece may be achieved with the use of a battery or transformer and rectifier power supply or rotating machine device as is also commonly known in the electrical art. The magnitude of the established current flow can be adjusted to provide a varying sensitivity for the FIG. 1 sequence that is, a variation in the smallest detectable flaw in the workpiece. The upper limit acceptable for the workpiece current flow is determined by the tolerable $I^2R$ heating of the workpiece work area surface and electrode attachment regions. The acceptable degree of workpiece heating is in turn determined by the temperature limitations of the liquid crystal materials and the metals and other materials in the workpiece and adjacent the workpiece. A fuel tank containing a mixture of fuel vapor and air would require some care in limiting work area temperatures and in precluding elecrode sparks, for example. The type of material being tested for flaws and its electrical resistivity of course influence the workpiece current flow magnitude resulting from a given amount of workpiece voltage drop. The mathematical product of the current and voltage levels determines the power dissipation and heat developed in the workpiece. Workpiece temperature can be limited through the use of non-continuous or pulsed workpiece currents with the required current pulse duration being determined by the time response of the liquid crystal cell and the observer's eye response time. Artificial cooling of the workpiece may also be employed if needed.

Disturbance from an otherwise uniform alignment of the liquid crystal particles is, of course, induced by the electric field around a flaw, and the electrical potential drop across the flaw. The electric field strength needed to achieve an alignment response from a particular liquid crystal solution for a given size of work area flaw is determined by the alignment response threshold for the liquid crystal solution used and can be varied within a limited range as is known in the liquid crystal art.

In block 106 of the FIG. 1 sequence, illumination of the work area surface is achieved; such illumination can be accomplished with either natural sunlight or artificial light. An artificial light illumination source of the elevated energy state type, that is, of the incandescent and gaseous discharge types is preferred. Such artificial illumination can within these bounds be provided by a mercury vapor lamp, a fluorescent lamp, a laser device or a heated filament incandescent lamp, or by other lamps such as an arc lamp which are known in the electrical art. Location and orientation of the light source is generally not critical for liquid crystal cell use and suitable illumination can usually be achieved with a light source location somewhere over the work area surface.

Block 108 of FIG. 1 describes a visual inspection sequence for detecting perturbations in the pattern of the liquid crystals applied in block 102. This inspection may be achieved with the aid of magnifying optics where the work surface flaws of interest are small in size and are not enlarged to an adequate degree by the current flow adjustments described above in connection with block 104. Use of a magnifying device in the block 108 visual inspection step of the FIG. 1 sequence may enable transmission of work area surface illumination through the magnifying device lenses.

Although the FIG. 1 described inspection sequence is desirable for many workpiece forms, the application of a liquid crystal solution or suspension in block 102 implies orientation of the workpiece surface in a near horizontal position and the presence of a planar area in the work area surface or the presence of conditions not greatly departed from these. These conditions are desirable and provide a high degree of flaw detection sensitivity using the liquid crystal inspection sequence; an alternate arrangement, however, as shown in FIG. 2 and FIG. 2A of the drawings may be more useful in some versions of the invention.

Figure 2:
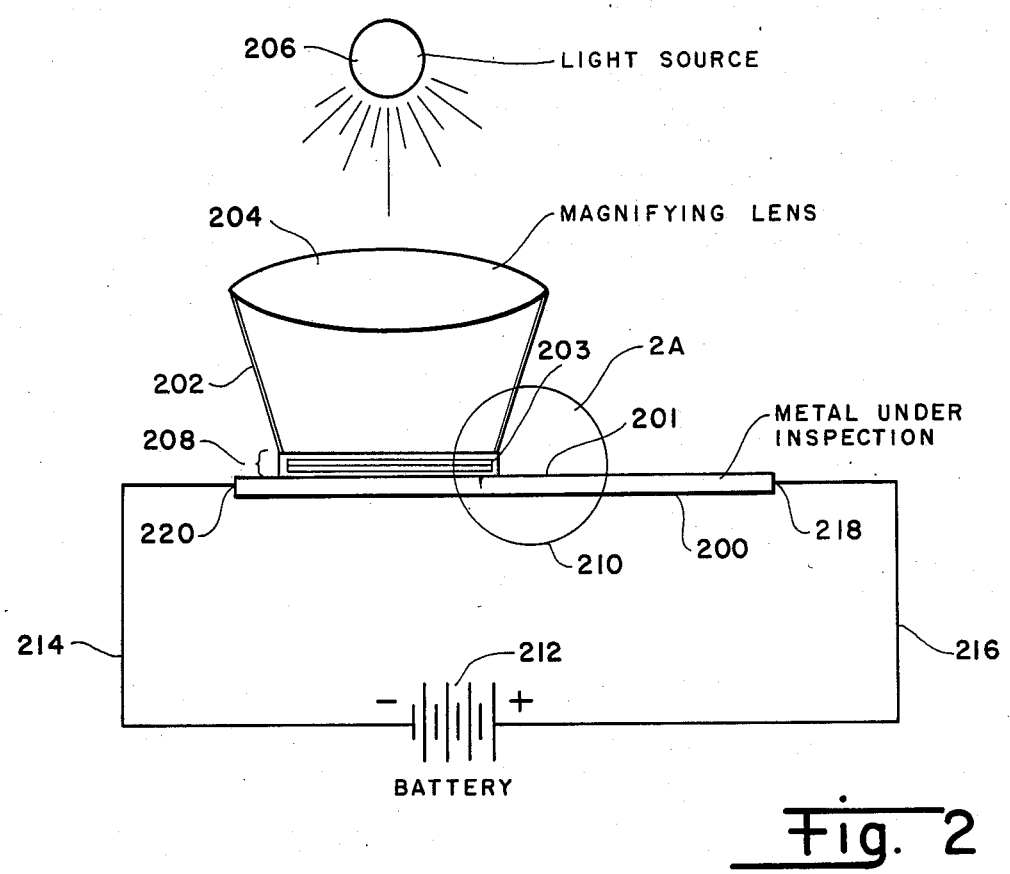
FIG. 2 is a self-contained indicator arrangement of the invention.

In the FIG. 2 arrangement of the inspection apparatus, the liquid crystal solution or suspension, which is indicated at 224, is contained within a substantially closed chamber. This chamber, 203, is made optically transparent in nature along at least one of its enclosure surfaces. The transparent surface is indicated at 222 in FIG. 2. In the FIG. 2 version of the invention, the workpiece recited in the block 100 in FIG. 1 is shown at 200, the work area surface of the workpiece is indicated at 201 and the electrodes for establishing current flow in the workpiece are indicated at 218 and 220. Current flow through the workpiece 200 in FIG. 2 is induced by the electrodes 218 and 220 from a pair of leads 214 and 216 which connect the workpiece to an energy source such as the battery 212. The workpiece 200, work area surface 201, battery 212, leads 214 and 216, and electrodes 218 and 220 are therefore similar in nature to the devices which would be employed in performing the FIG. 1 inspection sequence. In similar fashion, a light source 206 as would be employed in the step 106 in FIG. 1 is shown in FIG. 2 and a magnifying lens 204 as would be used in the inspection step 108 in FIG. 1 is also shown in FIG. 2. The magnifying lens 204 in FIG. 2 is shown to be supported on a frame member 202 which may be fabricated of wire or transparent plastic or any of a number of suitable materials known in the art. The light source 206 may, of course, be located to the side of the magnifying lens 204 so that illumination of the work area surface 201 occurs through the frame member 202. The magnifying lens 204 may also be hand-held with a self contained light source 206 or employ other means to obtain a variable magnification.

Figure 2A:
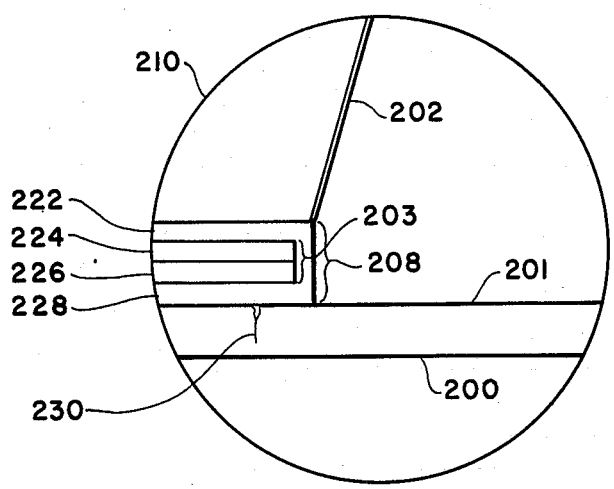
FIG. 2A shows a portion of the FIG. 2 apparatus in expanded form.

The liquid crystal solution or suspension and the contrasting color background material are incorporated into the optically transparent portable wafer 208 in FIG. 2; details of this wafer and the area surrounded by the circle 210 are shown in the lower expanded portion of FIG. 2, identified as FIG. 2A. In this FIG. 2A expanded portion is shown the workpiece 200, the work area surface 201, the frame member 202, and the elements included within the optically transparent portable wafer 208. These wafer-incorporated elements include the layer of light absorbing material 226 which may be of the paint or other variety of coloring materials as was described in connection with block 100 in FIG. 1. The liquid crystal solution or suspension is indicated at 224 in FIG. 2A. The relative thicknesses of the light absorbing material 226, the liquid crystal material 224, and the transparent surface material 222 are not shown to scale in FIG. 2 or FIG. 2A, and may vary according to the materials used. The liquid crystal image may also be enhanced through the use of polarizers, filters, and other devices known to the optics art.

The back side closure portion 228 of the optically transparent portable wafer 208 can also be fabricated from transparent material, as is indicated by the absence of a dividing line between the transparent surface material 222 and the back side closure portion 228 in FIG. 2A, or alternately, may be composed of a different type of material which is joined to the transparent surface material in a bonded or otherwise fabricated joint. Optical transparency for the back side closure portion 228 is, of course, not necessary. In an alternate FIG. 2 related arrangement, light-absorbing material could be applied directly to the surface to be inspected and the liquid crystals contained between two transparent sheets—this arrangement resulting in reusability of the liquid crystal and transparent sheet wafer.

The thickness of the back side closure material 228 is interposed between the work area surface 201 and the liquid crystal material 224, and therefore has a tendency to diminish the sensitivity of the work area surface fault indication by way of distancing the liquid crystal particles from the source of the aligning electrical field. The degree of desensitizing realized with the FIG. 2 structure may be moderated by the use of a thin back side closure member 228 and by controlling the thickness of the light absorbing material 226. Generally, however, the FIG. 2 apparatus will be somewhat less sensitive to surface flaws than will an inspection procedure accomplished according to the FIG. 1 sequence. Use of the FIG. 2 apparatus with non-planar workpieces also increases the sensitivity degradation for instances where the transparent portable wafer 208 cannot be located immediately adjacent the work surface 201 current path and electric field because of the presence of surface irregularities. For the portion of the work surface which comes in contact with the back side closure member 228, this surface irregularity desensitizing is minimal. The word contiguous or contiguum may be used to describe arrangements of this type wherein the liquid crystal material is located as closely as possible in practicality to the current conducting workpiece 200 and the electric field source considering the necessary intervention of light absorbing material 226 and the back side closure member 228, or in the case of the FIG. 1 sequence, the presence of light absorbing material applied in the block 100.

Although the use of direct current energy as indicated by the battery 212 in FIG. 2 is preferred for the NDI arrangement described herein, the use of alternating current energy and the induction of current flow into the workpiece 200 by way of magnetic coupling from a source of undulating or alternating magnetic flux is also possible. With such non-direct current flow the electric fields attending current flow in the workpiece will also be undulating or alternating in nature. Although fields of this type are not so desirable for use with liquid crystal dispays as are direct current fields, some indication of surface flaws can be achieved with such energization. Use of alternating current or undulating current energy induced by magnetic coupling is more convenient for most inspection scenarios, since electrodes and good electrical contact with the workpiece are not required with such magnetic coupling.

While the apparatus and method herein described constitute a preferred embodiment of the invention, it is to be understood that the invention is not limited to this precise form of apparatus or method, and that changes may be made therein without departing from the scope of the invention, which is defined in the appended claims.

I claim:

1. A method for detecting the presence of physical defect flaws in work area surface and subsurface portions of a nominally uniform electrically bulk conductive non-ferrous workpiece comprising the steps of:
    coloring the work area surface of said workpiece to provide an optical contrast background;
    disposing a suspension of liquid crystal particles over said optical contrast background located in contiguum with said work area surface of said electrically bulk conductive non-ferrous workpiece;
    establishing an electrical potential difference across said workpiece work area surface to establish an electrical current flow through said workpiece in a direction substantially parallel with said work area surface, a portion of said potential difference being perturbed from a uniform potential change pattern across each of said physical defect flaws;
    illuminating said work area liquid crystal suspension with visible spectrum optical energy; and
    visually inspecting the optical image reflected by said liquid crystal suspension and said optical contrast background for said electric potential pattern induced liquid crystal pattern perturbations, said perturbations thereby identifying said work area surface and subsurface defects.

2. The method of claim 1 wherein said disposing step additionally includes the steps of:
    coating the to-be-examined work area surface of said workpiece with said optical contrast background coating; and
    applying a suspension of liquid crystal particles to said coated work area surface.

3. The apparatus of claim 1 wherein said nominally uniformly electrically conductive workpiece is comprised of metal.

4. The method of claim 3 wherein said electrical current flow is a flow of direct current.

5. The method of claim 4 wherein said illuminating step includes flooding the surface of said work area with artificial light.

6. The method of claim 5 wherein said work area coating step includes painting said work area surface with a dark colored paint.

7. The method of claim 1 wherein said disposing step additionally includes the steps of:
    enclosing said suspension of liquid crystal particles and said optical contrast background within an optical transparency portable wafer; and
    disposing said portable wafer adjacent said work area surface within the influence of an electric field attending said potential difference.

8. The method of claim 7 wherein said electrical potential difference is a direct current potential difference and wherein said direct current potential difference extends laterally across said work area surface and produces a direct current flow parallel to said work area surface within a body portion of said workpiece.

9. The method of claim 8 wherein said illuminating step includes flooding said work area surface with sunlight.

10. The method of claim 8 wherein said illuminating step includes flooding said work area surface with artificial light.

11. The method of claim 1 wherein said step of establishing an electrical potential difference includes magnetically coupling said work member with a source of varying magnetic flux.

12. A method for detecting surface defects in a work area surface of a homogeneous electrically conductive non-ferrous metallic workpiece comprising the steps of:
coloring the to-be-inspected work area surface of said homegeneous metallic non-ferrous workpiece with an optical contrast material of a first color;
attaching a first electrode to said work member in a location adjacent one boundary of said work area surface;
connecting a second electrode to said work member in a location adjacent an opposite boundary of said work area surface;
establishing an electrical direct current flow between said first and second electrodes in said homogeneous workpiece, said current flow traversing said work area surface and flowing along a workpiece path parallel thereto.
covering said colored work area surface with a liquid crystal suspension layer capable of transmitting optical energy to and from said optical contrast material in a first electric field responsive crystal alignment state thereof and of reflecting second color optical energy in a second electric field absent crystal alignment state thereof;
illuminating said work area surface and said liquid crystal suspension layer with visible spectrum optical energy from an optical source of the elevated energy state type; and
visually examining a magnified optical image from said illuminated liquid crystal suspension layer for electric potential gradient change responsive discontinuities involving said first and second colors.

13. Apparatus for detecting surface defects in a work area surface of a uniform bulk conductive metallic non-ferrous workpiece comprising:
coloration means for covering said uniform metallic non-ferrous workpiece work surface with a film of first color
first electrode means for conducting electrical energy to a workpiece location adjacent one boundary of said work area surface;
second electrode means for conducting electrical energy to a workpiece location adjacent an opposite boundary of said work area surface;
electrical current generating means connected with said first and second electrode means for establishing within said metallic workpiece an electrical direct current flow traversing said work area surface in a direction substantially parallel therewith;
liquid crystal suspension means for covering said covered work surface with a layer capable of transmitting optical energy to and from said first color material in a first crystal alignment state thereof and of reflecting second color optical energy in a second crystal alignment state thereof;
electrical energy to optical energy transducer means of the elevated energy state type for illuminating said work area surface and said liquid crystal suspension means layer with visible spectrum optical energy; and
means for visually examining the optical image from said illuminated liquid crystal suspension means for electrical potential variation responsive perturbations between said first and second colors.

* * * * *